United States Patent [19]
Hofs et al.

[11] Patent Number: 5,300,708
[45] Date of Patent: Apr. 5, 1994

[54] PROCESS FOR THE CATALYTIC HYDROGENATION OF ORGANIC COMPOUNDS IN THE GAS PHASE

[75] Inventors: Wolfgang Hofs, Oberhausen; Thomas Muller, Dinslaken, both of Fed. Rep. of Germany

[73] Assignee: Hoechst Aktiengesellschaft, Fed. Rep. of Germany

[21] Appl. No.: 81,682

[22] Filed: Jun. 23, 1993

[30] Foreign Application Priority Data

Jun. 25, 1992 [DE] Fed. Rep. of Germany ....... 4220783

[51] Int. Cl.$^5$ ................ C07C 29/141; C07C 31/20; F16F 1/34
[52] U.S. Cl. .................... 568/853; 165/71; 568/862; 568/881
[58] Field of Search ............ 568/953, 862, 881

[56] References Cited

U.S. PATENT DOCUMENTS

| | | | |
|---|---|---|---|
| 2,771,493 | 11/1956 | Jacks et al. | 568/881 |
| 3,340,312 | 9/1967 | Duke et al. | 568/853 |
| 3,939,216 | 2/1976 | Wright | 568/853 |
| 4,626,604 | 12/1986 | Hiles et al. | 568/881 |
| 5,233,099 | 8/1993 | Tabata et al. | 568/853 |

FOREIGN PATENT DOCUMENTS 73129 3/1983 European Pat. Off. ............ 568/881

Primary Examiner—Joseph E. Evans
Attorney, Agent, or Firm—Jordan B. Bierman

[57] ABSTRACT

A process for the catalytic hydrogenation of organic compounds in the gas phase. The reaction product-containing circulating gas leaving the hydrogenation reactor is compressed without prior cooling, and is then used to heat the starting materials in a superheater to the reaction temperature. The circulating gas stream is further cooled in a hot-gas heat exchanger by cold reactants in a counter-current manner; as a result, substantially all the reaction product condenses out leaving recycle gas. After addition of fresh gas and starting material, the recycle gas is returned via a purification column to the hydrogenation reactor.

7 Claims, 2 Drawing Sheets

PROCESS FOR THE CATALYTIC HYDROGENATION OF ORGANIC COMPOUNDS IN THE GAS PHASE

The invention relates to the catalytic hydrogenation of organic compounds, in particular the gas phase hydrogenation of aldehydes and hydroxyaldehydes to give monohydric or polyhydric alcohols.

BACKGROUND OF THE INVENTION

In industrial practice, the hydrogenation of organic compounds, such as saturated and unsaturated aldehydes or hydroxyaldehydes, is generally carried out continuously, using excess hydrogen. Unreacted hydrogen is recirculated (circulating gas) into the hydrogenation reactor, usually after a part of the hydrogen, laden with inert and ballast substances, has been separated, and the amount separated plus the amount consumed has been replaced by fresh gas.

The overall process conventionally proceeds as set forth below, variations or adaptations to individual requirements obviously being possible. Hydrogen in the form of fresh gas and circulating gas is compressed to overcome the pressure drop existing in the system. At the same time, but separate from each other, hydrogen and the starting material to be hydrogenated are fed to a heat exchanger. Here, the reactants are preheated by the reaction product and, if they are not already in the gaseous state, are at least partially vaporized, while the reaction product is cooled and higher-boiling components thereof condensed out.

The non-vaporized reactants can be converted into the gas phase in a subsequent heat exchanger, except for a small liquid portion which is withdrawn, and finally heated in a superheater to the reaction temperature and fed to the reactor. Here, the hydrogenation is carried out at substantially constant temperature, and the heat liberated during this hydrogenation is utilized for steam generation. The hot product passes into the above-mentioned heat exchanger and then into a condenser. A hydrogenation process proceeding approximately in the stages outlined above is described, for example, in Ullmanns Encyklopadie der technischen Chemie [Ullmann's Encyclopedia of Industrial Chemistry], 3rd Edition (1953), pp 778, 779 for the hydrogenation of crotonaldehyde to give butanol.

In practice, it is of essential importance to organize the heat balance of the overall process to achieve as high a degree of energy efficiency as possible. Furthermore, the activity of the catalyst should not be damaged by foreign substances (in particular, higher boiling materials) which are carried over into the hydrogenation reactor by the gaseous reactants. For this purpose it is necessary, inter alia, to separate the by-products from the product stream entering into the hydrogenation reactor as completely as possible.

It has been shown that relatively high pressure drops in the hydrogenation plant lead to a rise in the gas outlet temperature at the compressor and, as a consequence thereof, impair the heat transfer at the heat exchanger. Furthermore, although it is known that a horizontal arrangement of the heat exchanger improves the condensation of the reaction product, it also decisively reduces the heat transfer on the tube side of the heat exchanger.

SUMMARY OF THE INVENTION

The object of the invention, therefore, is to develop a process for the hydrogenation of organic compounds which avoids the foregoing disadvantages.

A circulating gas, comprising hydrogen, the organic compound being reacted (hereinafter the organic compound), and the reaction product, exits the hydrogenation reactor and is compressed without prior cooling sufficiently to compensate for the pressure drop in the system. The circulating gas then flows through a superheater wherein the starting materials (fresh hydrogen, the organic compound, and recycled gas) are heated from an intermediate temperature to the reaction temperature. In doing so, the circulating gas is partially cooled.

The partially cooled circulating gas is then conducted to a hot-gas heat exchanger wherein it preferably flows countercurrent to the cold starting materials, heats the starting materials to the intermediate temperature, and is thereby further cooled to cause the circulating gas to form a liquid phase (the reaction product) and a gas phase (comprising the recycle gas). The reaction product is then conducted out of the system in a product stream. Fresh organic compound and hydrogen are added to the recycle gas to form more starting materials which are introduced into the hot-gas heat exchanger.

In a preferred form of the invention, the recycle gas and the organic compound are passed through a purification column after exiting the hot-gas heat exchanger and before entering the superheater. The fresh hydrogen, which does not have to be preheated as it is already a gas, is preferably introduced into the starting materials at the purification column, but may be introduced downstream thereof but upstream of the superheater.

When the recycle gas leaves the hot-gas heat exchanger, it may still contain some recoverable reaction product. Therefore, in another preferred embodiment, the gas phase passes through a condenser which causes additional reaction product to condense out, leaving the recycle gas. The condensed additional reaction product is directed to the product stream.

Thus, an outstanding utilization of both the energy supplied to the system and that generated therein is achieved. Furthermore, the process enables a sharp separation of the valuable reaction products and the by-products from the circulating gas. As a result, the catalyst is not poisoned, since the higher boiling substances are readily removed.

DETAILED DESCRIPTION OF THE INVENTION

The compression of the circulating gas after leaving the reactor increases its heat content by the heat of compression. Thus, thermal energy is utilized for heating the starting materials, for example the organic compound, hydrogen, and optionally the recycle gas, to the reaction temperature in the superheater. Maintaining a very low residence time avoids the possibility of the reaction product being thermally damaged. The circulating gas leaving the superheater passes into the hot-gas heat exchanger which is preferably designed as a falling-film evaporator. The circulating gas is intensively cooled by the starting materials flowing countercurrently, so that the hydrogenation product condenses out as a liquid phase and the starting materials evaporate to the gaseous state. A further reduction of the temperature of the gas stream may be achieved in a downstream condenser, in which the remaining hydrogenation product is separated out.

In order to restrict the content of inert and ballast substances, a small part of the recycle gas is separated off from the gas stream as exhaust gas. The far greater part of the recycle gas, essentially hydrogen and, in addition to some inert and ballast substances, small amounts of non-condensable reaction products, is returned to the hot gas heat exchanger, mixed with fresh starting materials, and thereafter preferably introduced into the purification column. Here, the starting materials stream is rectified using a plurality of equilibrium stages. In a preferred embodiment, there is a water separator downstream of the hot-gas heat exchanger. This device completes the condensation of all higher-boiling components of the starting materials stream. The use of a purification column in the process according to the invention ensures that components which boil higher than the hydrogenation product do not pass into the reactor and thus do not poison the catalyst. For best results, the fresh hydrogen, which replaces that consumed in the hydrogenation, is introduced into the reboiler of the purification column; there it reduces the boiling temperature and thus protects the product. It is then fed to the superheater and subsequently to the hydrogenation reactor as part of the starting materials.

According to another preferred embodiment of the process according to the invention, the hot-gas heat exchanger used is a falling-film evaporator constructed in a particular manner, in which the mass streams are countercurrent to each other, an unconventional mode of operation for this type of apparatus. Therefore, particular measures are necessary in order to optimize the heat transfer on the shell side of the exchanger tubes. According to the invention, the tubes are preferably furnished on the outside with spiral grooves or wire coils. Because of its surface tension, the liquid collects at the grooves or wire coils, so that there is substantial available exchange surface for condensation. The deflection baffles on the heat exchanger tubes are designed to double as condensate collectors. Each baffle has an outlet via a down pipe which carries the condensate to the discharge chamber at the foot of the heat exchanger.

BRIEF DESCRIPTION OF THE DRAWINGS

In the accompanying drawings, constituting a part hereof, and in which like reference characters constitute like parts.

DETAILED DESCRIPTION OF THE DRAWINGS

Figure 1:
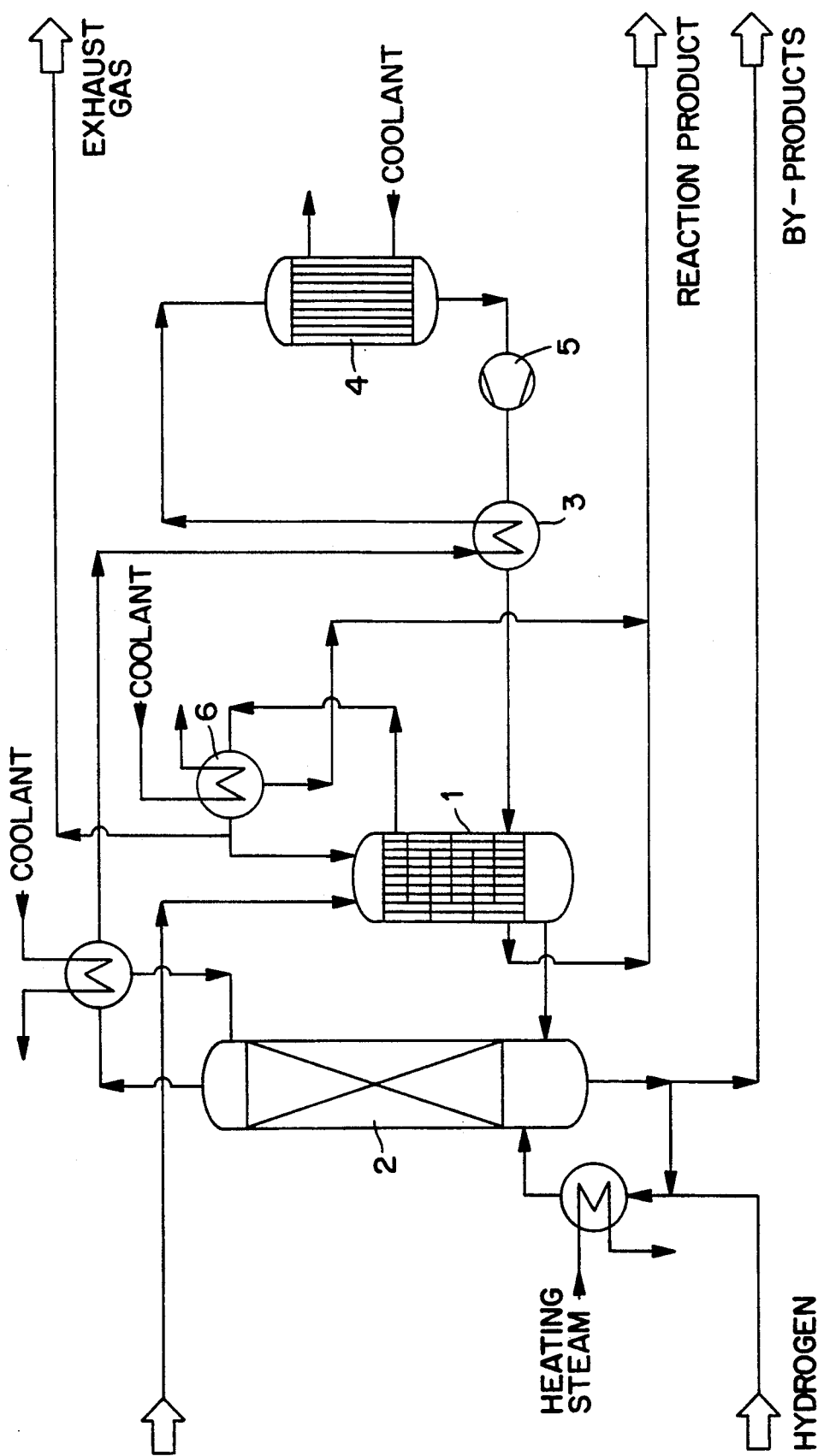
FIG. 1 is a diagrammatic representation of the novel process.

In the process according to FIG. 1, the starting materials (the organic compound to be hydrogenated and the recycle gas) are heated in hot-gas heat exchanger 1 by partially cooled circulating gas flowing counter-currently and fed via purification column 2, where fresh hydrogen is added, to superheater 3. The mixture is heated in superheater 3 to the reaction temperature and reacted in reactor 4 to form the circulating gas (containing the reaction product) which is compressed in compressor 5 to overcome the pressure drop in the system.

After cooling in superheater 3 (by heating the starting materials to their reaction temperature), the circulating gas is then fed to hot-gas heat exchanger 1 wherein it is cooled further (by heating the starting materials to their intermediate temperature) and condensed, thereby separating into a gas phase (recycle gas) and a liquid phase (reaction product). The gas phase is passed into condenser 6 which causes further condensation of reaction product. The recycle gas from condenser 6 is returned to hot-gas heat exchanger 1 and fresh hydrogen and organic compound are replenished.

Figure 2:
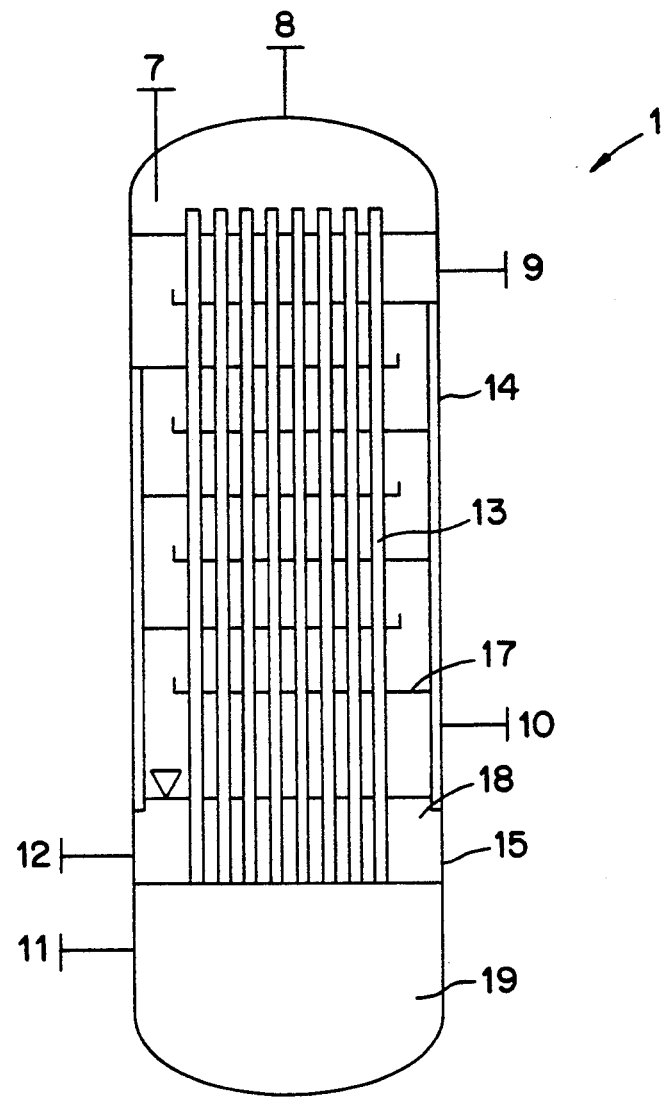
FIG. 2 is a schematic view of a preferred embodiment of the hot-gas heat exchanger of the invention.

In hot-gas exchanger 1, as shown in FIG. 2, partially cooled reaction product enters the apparatus via product inlet 10. With the aid of deflection baffles 17, it is conducted in a cross-countercurrent direction against the liquid and gaseous cold starting materials which are introduced via organic component inlet 7 and recycle inlet 8. The liquid starting materials are caused to form a thin film on the inner sides of tubes 13 by known distribution devices.

The partially cooled reaction product, which is at or near its dew point, transfers its heat to the cold starting materials and thereby partially condenses, while the liquid portion of the starting materials evaporates. The heated starting materials leave the apparatus via starting materials outlet 11 in well 19. The cooled reaction product is withdrawn as the gas phase through gas outlet 9 and as the liquid phase through liquid outlet 12. By observing the described measures, the outlet temperature of the starting materials may be maintained higher than the outlet temperature of the reaction products. With the aid of a hot-gas heat exchanger of the type shown in FIG. 2, condensation occurs in a very short space, and thin condensation films are assured, both of which contribute to good heat transfer. For this purpose, the condensate is diverted by deflection baffles 17, which also serve as receivers, into down pipes 14 which carry it to discharge chamber 18 for withdrawal through outlet 12.

Figure 3:
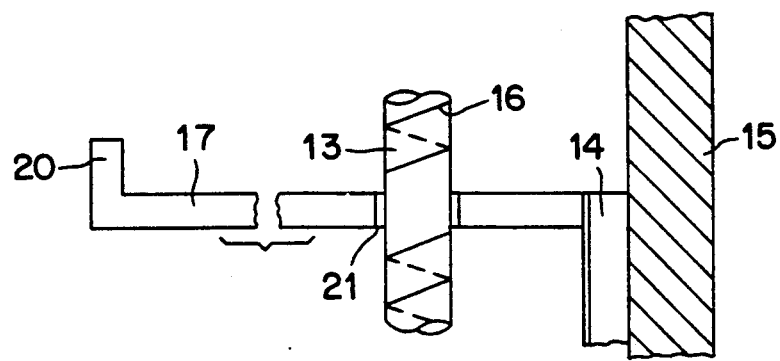
FIG. 3 is an enlarged, partially fragmented, schematic view of the heat exchange tubes and baffles of the hot-gas heat exchanger.

FIG. 3 shows the details of the construction of deflecting baffle 17 having vertical lip 20 remote from pipes 14 for collecting the condensate, seal 21 to prevent condensate from leaking between baffle 17 and tubes 13, and pipe 14 to receive and discharge the condensate into chamber 15. Tube 13 has condensate collection aids 16 on its outer surface, e.g. in the form of spiral grooves or wire coils which increase the available condensation surface area.

EXAMPLE

A test is carried out according to Diagram 1. The starting material is 2.2-dimethyl-3-hydroxypropanal which is reacted with hydrogen to give 2.2-dimethyl-3-propane diol; 125.8 kcal heat per kg of starting material are set free. For purification of the reaction product, 20.6 kcal/kg energy in the form of heat must be fed into the purification column. The circulating gas contains 20.3% by weight of reaction product, 12.7% by weight of hydrogen, 12.5% by weight of water, 15.4% by weight of isobutanol and 39% by weight of inerts.

On performing hydrogenation under state-of-the-art conditions, 252 kcal energy in the form of heat per kg of starting material are to be fed into the purification column, i.e. over 12 times more than in the process according to the invention. Furthermore, the circulating gas contains a significantly higher proportion of foreign materials, i.e. 2.36% by weight related to the starting material, whereas the proportion is 66 ppm by weight in the inventive process.

What we claim is:

1. A process for catalytic hydrogenation of an organic compound in a gas phase, said organic compound being mixed with recycle gas containing hydrogen, said process comprising warming said compound and said recycle gas from their starting temperatures to an intermediate temperature in a first heat exchange zone, introducing additional hydrogen into said compound and said recycle gas to form a starting material, heating said starting material from said intermediate temperature to a reaction temperature in a second heat exchange zone, introducing said starting material into a reaction zone at said reaction temperature, wherein said organic compound is hydrogenated to a reaction product, thereby forming circulating gas which includes said reaction product, said organic compound, and hydrogen, withdrawing said circulating gas from said reaction zone, compression of said circulating gas without prior cooling thereof, passing said circulating gas through said second heat exchange zone, whereby said circulating gas transfers heat to said starting materials, to cool said circulating gas and to cause said heating, passing partially cooled said circulating gas through said first zone whereby said circulating gas causes said warming and is further cooled to cause said circulating gas to form a liquid phase, containing said reaction product, and a gas phase, comprising said recycle gas, and blending said recycle gas with said compound.

2. The process of claim 1 wherein said compression is sufficient to compensate for pressure losses in said process.

3. The process of claim 1 wherein said partially cooled circulating gas passes through said first zone in a direction countercurrent to that of said compound and said recycle gas.

4. The process of claim 1 wherein said compound and said recycle gas pass through a purification zone upstream of said first heat exchange zone.

5. The process of claim 4 wherein additional hydrogen is introduced into a reboiler zone of said purification zone.

6. The process of claim 1 wherein said gas phase is further cooled in a condensing zone downstream of said first zone, whereby additional reaction product is condensed out.

7. The process of claim 1 wherein said organic compound is selected from the group consisting of saturated aldehydes, unsaturated aldehydes, and hydroxy aldehydes.

* * * * *